(12) United States Patent
Arruda et al.

(10) Patent No.: US 9,259,510 B2
(45) Date of Patent: *Feb. 16, 2016

(54) SYSTEM AND METHOD FOR FORMING BONE, LIGAMENT, AND BONE-LIGAMENT CONSTRUCTS

(71) Applicant: The Regents of the University of Michigan, Ann Arbor, MI (US)

(72) Inventors: Ellen M. Arruda, Ann Arbor, MI (US); Lisa M. Larkin, Ann Arbor, MI (US); Fatima N. Syed-Picard, Portage, MI (US); Michael Smietana, Orion, MI (US); Jinjin Ma, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/267,439

(22) Filed: May 1, 2014

(65) Prior Publication Data

US 2014/0243979 A1    Aug. 28, 2014

Related U.S. Application Data

(63) Continuation of application No. 12/025,151, filed on Feb. 4, 2008, now Pat. No. 8,764,828.

(60) Provisional application No. 60/889,178, filed on Feb. 2, 2007.

(51) Int. Cl.

| A61L 27/38 | (2006.01) |
|---|---|
| A61F 2/28 | (2006.01) |
| A61F 2/08 | (2006.01) |
| C12N 5/077 | (2010.01) |
| A61L 27/36 | (2006.01) |
| A61K 35/12 | (2015.01) |
| C12N 5/0775 | (2010.01) |

(52) U.S. Cl.
CPC .............. *A61L 27/3608* (2013.01); *A61F 2/08* (2013.01); *A61F 2/28* (2013.01); *A61L 27/386* (2013.01); *A61L 27/3834* (2013.01); *A61L 27/3847* (2013.01); *C12N 5/066* (2013.01); *C12N 5/0654* (2013.01); *A61F 2002/2867* (2013.01); *A61K 35/12* (2013.01); *C12N 5/0663* (2013.01); *C12N 2500/32* (2013.01); *C12N 2500/38* (2013.01); *C12N 2501/115* (2013.01); *C12N 2501/15* (2013.01); *C12N 2501/39* (2013.01); *C12N 2533/52* (2013.01)

(58) Field of Classification Search
None
See application file for complete search history.

(56) References Cited

U.S. PATENT DOCUMENTS

| 3,960,151 A | 6/1976 | Kuhn |
|---|---|---|
| 4,605,623 A | 8/1986 | Malette et al. |
| 4,642,292 A | 2/1987 | Reid et al. |
| 4,759,764 A | 7/1988 | Fawcett et al. |
| 4,776,853 A | 10/1988 | Klement et al. |
| 4,801,299 A | 1/1989 | Brendel et al. |
| 4,870,966 A | 10/1989 | Dellon et al. |
| 4,940,853 A | 7/1990 | Vandenburgh |
| 4,963,146 A | 10/1990 | Li |
| 5,019,087 A | 5/1991 | Nichols |
| 5,026,381 A | 6/1991 | Li |
| 5,147,399 A | 9/1992 | Dellon et al. |
| 5,153,136 A | 10/1992 | Vandenburgh |
| 5,366,616 A | 11/1994 | Skeels et al. |
| 5,443,950 A | 8/1995 | Naughton et al. |
| 5,452,236 A | 9/1995 | Lintilhac et al. |
| 5,618,718 A | 4/1997 | Auger et al. |
| 5,700,688 A | 12/1997 | Lee et al. |
| 5,756,350 A | 5/1998 | Lee et al. |
| 5,840,689 A | 11/1998 | Daniloff |
| 5,879,383 A | 3/1999 | Bruchman et al. |
| 5,882,929 A | 3/1999 | Fofonoff et al. |
| 6,033,660 A | 3/2000 | Mather et al. |
| 6,095,148 A | 8/2000 | Shastri et al. |
| 6,114,164 A | 9/2000 | Dennis et al. |
| 6,207,451 B1 | 3/2001 | Dennis et al. |
| 6,214,021 B1 | 4/2001 | Hadlock et al. |
| 6,241,981 B1 | 6/2001 | Cobb et al. |
| 6,303,286 B1 | 10/2001 | Dennis et al. |
| 6,448,076 B2 | 9/2002 | Dennis et al. |
| 6,537,567 B1 | 3/2003 | Niklason et al. |
| 6,689,161 B2 | 2/2004 | Chen et al. |
| 6,777,234 B1 | 8/2004 | Dennis et al. |
| 7,338,798 B2 | 3/2008 | Dennis et al. |
| 2001/0049138 A1 | 12/2001 | Dennis et al. |
| 2002/0115208 A1 | 8/2002 | Mitchell et al. |
| 2004/0132184 A1 | 7/2004 | Dennis et al. |

(Continued)

OTHER PUBLICATIONS

Calve et al., Engineering of functional tendon, Tissue Eng., 10(5-6):755-61 (2004).
Ducheyne et al., Bioactive ceramics: the effect of surface reactivity on bone formation and bone cell function, Biomaterials, 20(23-24):2287-303 (1999).
Goh et al., Tissue-engineering approach to the repair and regeneration of tendons and ligaments, Tissue Eng., 9 Suppl 1:S31-44 (2003).
Hairfield-Stein et al., Development of self-assembled, tissue-engineered ligament from bone marrow stromal cells, Tissue Eng., 13(4):703-10 (2007).
International Search Report for PCT/US08/52915, dated Aug. 8, 2009.
Ishaug et al., Bone formation by three dimensional stromal osteoblast culture in biodegradable polymer scaffolds, J. Biomed. Mater. Res., 36:17 (1997).
Khademhosseini et al., Microscale technologies for tissue engineering and biology, Proc. Natl. Acad. Sci. USA, 103(8):2480-7 (2006).
Kosnik et al., Functional development of engineered skeletal muscle from adult and neonatal rats, Tissue Eng., 7:573-84 (2001).

(Continued)

*Primary Examiner* — H. Sarah Park
(74) *Attorney, Agent, or Firm* — Marshall, Gerstein & Borun LLP

(57) ABSTRACT

A system and method for forming a bone construct include providing bone marrow stromal cells on a substrate without disposing the cells within an exogenous scaffold, and culturing the cells in vitro in osteogenic media such that the cells form a confluent monolayer and detach from the substrate to form a self-organized three-dimensional bone construct. A system and method for forming a ligament construct using fibrogenic media and a system and method for forming a functionally integrated bone-ligament construct are also provided.

19 Claims, 13 Drawing Sheets

(56) References Cited

U.S. PATENT DOCUMENTS

| | | |
|---|---|---|
| 2005/0053585 A1 | 3/2005 | Black et al. |
| 2005/0125049 A1 | 6/2005 | Brown et al. |
| 2006/0141620 A1 | 6/2006 | Brown et al. |
| 2011/0177134 A1 | 7/2011 | Harmon et al. |

OTHER PUBLICATIONS

Liu et al., The interaction between a combined knitted silk scaffold and microporous silk sponge with human mesenchymal stem cells for ligament tissue engineering, Biomaterials, 29(6):662-74 (2008).

Locklin et al., Effects of TGFbeta and bFGF on the differentiation of human bone marrow stromal fibroblasts, Cell Biol. Int., 23(3):185-94 (1999).

Marolt et al., Bone and cartilage tissue constructs grown using human bone marrow stromal cells, silk scaffolds and rotating bioreactors, Biomaterials, 27:6138-49 (2006).

Moreau et al., Sequential growth factor application in bone marrow stromal cell ligament engineering, Tissue Eng., 11:1887-97 (2005).

Peter et al., Polymer concepts in tissue engineering, J. Biomed. Mater. Res., 43(4):422-7 (1998).

Petrigliano et al., Tissue engineering for anterior cruciate ligament reconstruction: a review of current strategies, Arthroscopy, 22(4):441-51 (2006).

Russell et al., Ascorbic acid requirement for optimal flexor tendon repair in vitro, J. Orthopaedic Res., pp. 714-719 (1991).

Salgado et al., Bone tissue engineering: state of the art and future trends, Macromol. Biosci., 4(8):743-65 (2004).

Stoltz et al., Cell and tissue engineering and clinical applications: an overview, Biomed. Mater. Eng., 16(4 suppl):S3-S18 (2006).

Verhof et al., Bone formation in transforming growth factor beta-1-coated porous poly(propylene fumarate) scaffolds, J. Biomed. Mater. Res., 60(2):241-51 (2002).

Wang et al., Engineering of extensor tendon complex by an ex vivo approach, Biomaterials, 29(20):2954-61 (2008).

Wang et al., Role of osteoblast-fibroblast interactions in the formation of the ligament-to-bone interface, J. Orthrop. Res., 25(12):1609-20 (2007).

Zhou et al., Combined marrow stromal cell-sheet techniques and high-strength biodegradable composite scaffolds for engineered functional bone grafts, Biomaterials, 28(5):814-24 (2007).

Zhou et al., In vitro bone engineering based on polycaprolactone and polycaprolactone-tricalcium phosphate composites, Polym. Int., 56:333 (2007).

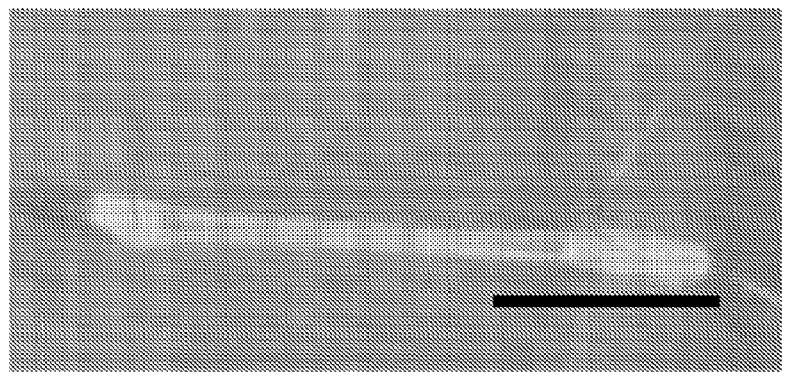
FIGURE 10a
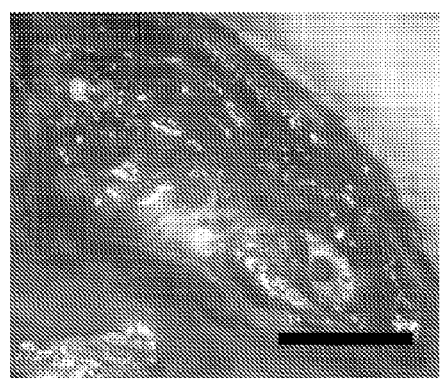 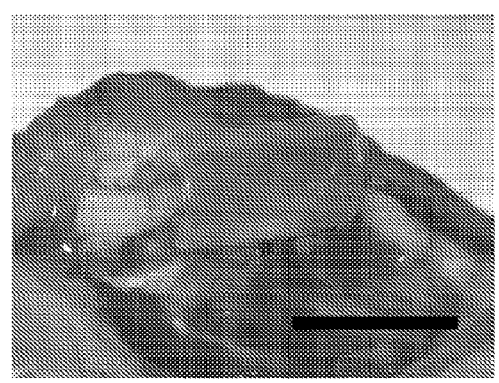
FIGURE 10b  FIGURE 10c
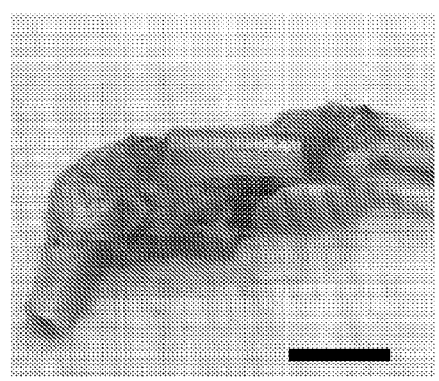 
FIGURE 10d  FIGURE 10e

SYSTEM AND METHOD FOR FORMING BONE, LIGAMENT, AND BONE-LIGAMENT CONSTRUCTS

CROSS-REFERENCE TO RELATED APPLICATIONS

This application claims the benefit of U.S. provisional application Ser. No. 60/899,178 filed Feb. 2, 2007, which is incorporated by reference herein.

STATEMENT REGARDING FEDERALLY SPONSORED RESEARCH OR DEVELOPMENT

The invention was made with government support under FA9550-05-1-0015 awarded by the Air Force Office of Scientific Research and CMS9988693 awarded by the National Science Foundation. The government has certain rights in the invention.

BACKGROUND OF THE INVENTION

1. Field of the Invention

This invention relates to tissue engineering, and more particularly to a system and method for producing engineered bone, ligament, and bone-ligament constructs.

2. Background Art

Bone is a vascularized tissue composed of a number of different types of cells. The tissue is predominately made up of a mineralized type I collagen matrix, and crystals within the mineralized matrix are composed of hydroxyapatite, a form of calcium phosphate. The three different types of cells in bone are osteoblasts, osteocytes, and osteoclasts. These cells each have different functions that allow bone tissue to continually remodel itself. Osteoblasts are the cells involved in the deposition and mineralization of type I collagen. These cells are round in morphology with cytoplasmic projections. Once the osteoblast is fully surrounded by mineralized matrix, it differentiates into an osteocyte. Osteocytes are cells that sit in open lacunae within mineralized bone. The functions of an osteocyte are to both resorb bone and to deposit new bone. Osteocytes are connected to other cells via cytoplasmic projections that can travel through channels within the mineralized matrix. Finally, osteoclasts are large multinucleated cells with large vacuoles that are involved in the bone resorption. Osteoclasts have two different types of plasma membranes: clear zones and ruffled borders. The ability of bone to remodel itself allows it to change its architecture and constitution (e.g. local density) with changes in its loading environment. Also, when fractured or inflicted with a small defect, bone can easily heal by the combination of processes of collagen deposition, mineralization, and resorption.

Ligaments are dense, relatively avascular connective tissues of the musculoskeletal system that help control joint motion, along with muscle. These tissues connect one bone to another and function to provide mechanical stability in joints, serve as a guide to joint motion, and prevent excess motion. About 80% by volume of ligament tissue is composed of longitudinally aligned collagen bundles. Most of the collagen is type I, however, type III is also present, as is elastin. Fibroblasts are the cellular component in ligaments and make up approximately 20% of the adult tissue volume. These cells attach to the individual collagen bundles and are elongated longitudinally.

The interface between bone and ligament is referred to as an enthesis. The purpose of the enthesis tissue is to transmit loads with high fidelity over a minimal volume of tissue from the compliant ligament to the stiff bone at the bone-ligament interface. This tissue is composed of four different zones that aid in the transition between the two vastly different tissues. The four zones of the enthesis are ligament, unmineralized fibrocartilage, mineralized fibrocartilage, and bone. The transition from ligament to unmineralized fibrocartilage is gradual, whereas a distinct boundary exists between unmineralized and mineralized fibrocartilage in adult tissue. This boundary is termed a tidemark and can be identified using hematoxylin and eosin (H and E) staining due to its extreme basophilic nature (Claudepierre and Voisin, *Joint Bone Spine* 72: 32, 2005; Benjamin et al., *J Anat* 208: 471, 2006). Fibrocartilage zones are composed of type II collagen and proteoglycans such as aggrecan, biglycan and decorin. The cells in fibrocartilage have the phenotype of chondrocytes, round and arranged in pairs or rows within lacunae. There are no molecular markers that are unique to this type of tissue, however, fibrocartilage, and in general the enthesis, is generally characterized by the presence of type II collagen due to the fact that this protein is not present in the neighboring ligament and bone tissues (Waggett et al., *Matrix Biol* 16: 457, 1998).

There are approximately one million surgeries each year in the United States that require bone and ligament grafts to replace tissue damaged by disease or extensive trauma. Several limitations are associated with grafting, such as graft availability, donor site morbidity, and immune rejection. Because of these complications, strategies are being developed to engineer bone and ligament tissue in vitro.

Current approaches to engineer bone and ligament involve the design of a three-dimensional (3D) scaffold that promote the differentiation and proliferation of osteogenic or fibroblastic cells and the deposition and mineralization of an osteogenic or fibroblastic extracellular matrix (ECM). The scaffold design rubrics also include the ability to withstand physiological loads in vivo and either the eventual incorporation into the native tissue or degradation during the course of tissue development (Salgado et al., *Macromol Biosci* 4: 743, 2004). Polymers such as poly(lactic-co-glycolic acid), poly(propylene fumarates), and poly(caprolactones) provide a matrix that promotes cell adhesion and migration, allow for the deposition and mineralization of osteogenic ECM in vitro, and have predictable degradation rates, but lack the mechanical properties needed to withstand the loads placed on natural bone in vivo (Ishaug et al, *J Biomed Mater Res* 36: 17, 1997; Vehof et al., *J Biomed Mater Res* 60: 241, 2002; Peter et al., *J Biomed Mater Res* 43: 422, 1998).

Hydroxyapatite and b-tricalcium phosphates are ceramics used for bone scaffolding that also promote cell adhesion and proliferation and, when implanted, have shown positive results in regards to bone regeneration in vivo. However, the brittle nature of ceramics inhibits their use in healing large defects (Salgado, 2004; Ducheyne and Qiu, *Biomaterials* 20: 2287, 1999). Polymer-ceramic composite scaffolds such as calcium phosphate salts embedded in poly(caprolactones) have been designed to mitigate the problems with using each material alone, but a significant percentage of cells fails to attach to the composite scaffold due to limited surface-to-volume ratio (Zhou et al., *Polym Int* 56: 333, 2007; Zhou et al., *Biomaterials* 28: 814, 2007). Single layer cell sheets grown from bone marrow stromal cells (BMSC) and wrapped around composite scaffolds have recently been shown to form constructs that resemble bone in vitro and in vivo (Zhou et al., *Biomaterials* 2007). However, this method still involves the use of an exogenous scaffolding that must incorporate into native tissue. Therefore, while scaffolding strategies appear to promote osteogenic or fibroblastic cell growth, limitations such as immune rejection, degradation, and nonphysiological mechanical properties of the scaffold need to be considered when used for bone and ligament repair.

BRIEF DESCRIPTION OF THE DRAWINGS

FIGS. 2a-c illustrate transmission electron microscopy (TEM) of EBC in vitro, wherein FIG. 2a depicts an osteoblast in an EBC having cytoplasmic projections (arrows) and surrounded by clusters of mineral (*) (scale bar=1.5 mm); FIG. 2b illustrates mineral clusters (*) at the center of the tissue where mineralization occurs through matrix vesicles (black arrows), and also depicts banded collagen I fibers with an approximate diameter of 30 nm (white arrows) (scale bar=200 nm); FIG. 2c shows mineralization also occurring through intrafibrillar calcification as seen by mineral crystals (arrows) along collagen fibrils (scale bar=200 nm)

FIGS. 5a-d illustrate TEM of an EBC explant according to the present invention, wherein FIG. 5a depicts an edge of the EBC has osteoprogenitor cells (black arrows) that are differentiating into osteoblasts (white arrows) indicating periosteum function (scale bar=8 mm); FIG. 5b illustrates an osteocyte sitting in lacuna within the bone matrix (scale bar=2 mm); FIG. 5c illustrates an osteoclast found in engineered bone resorbing demineralized bone matrix (BM) contains several nuclei (white arrows) and ruffled borders (black arrows), distinctions of this cell type (scale bar=10 mm); and FIG. 5d is a magnification of the boxed area of FIG. 5c which shows the ruffled border in more detail, illustrating the empty (*) and filled (arrows) vacuoles (scale bar=1 mm);

FIGS. 6a-c illustrate the fabrication of bone molds which may be used for formation of bone constructs with native bone dimensions according to the present invention, wherein FIG. 6a depicts a rat femur sprayed with silicone release and embedded in liquid silicone; FIG. 6b illustrates how, after the silicone has cured, the bone is cut form the silicone, leaving a 3-D mold of native bone as shown in FIG. 6c;

FIG. 10a is a photographs of a BLB construct according to the present invention;

FIGS. 10b-e are photographs of steps for MCL replacement according to the present invention, wherein FIG. 10b is a photograph after the MCL has been removed and holes have been drilled for BLB implantation; FIG. 10c depicts a BLB placed inside silicone tubing and secured in replacement of the excised MCL; FIG. 10d depicts a BLB construct within the silicone tubing one month following implantation; and FIG. 10e depicts the engineered BLB following one month implantation (black bar in each photograph represents 5 mm length);

FIGS. 11a-d illustrate the histology of BLB constructs according to the present invention explanted after one month following MCL replacement (sections were taken from the mid-section of the ligament portion of the explanted construct), wherein FIGS. 11a-b depict H & E staining of BLB constructs at two different magnifications, and FIGS. 11c-d depict immunostaining of BLB constructs with collagen type I and elastin, respectively.

DETAILED DESCRIPTION OF THE INVENTION

Figure 1A:
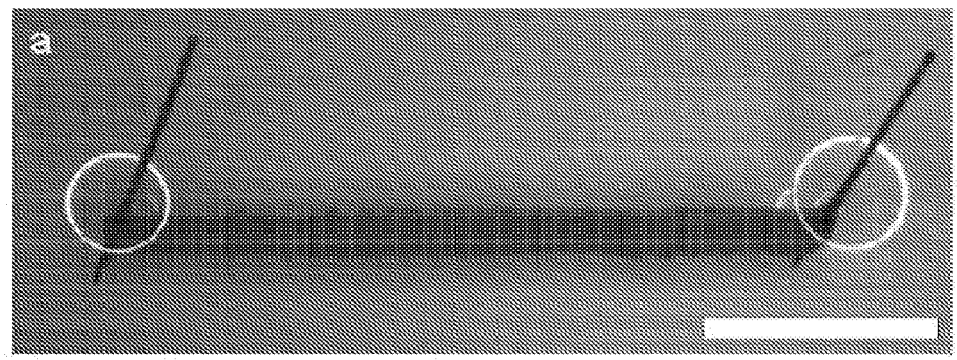
FIG. 1a is a photograph of an engineered bone construct (EBC) according to the present invention 7 days post 3D construct formation (scale bar=5 mm)

As required, detailed embodiments of the present invention are disclosed herein; however, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a representative basis for teaching one skilled in the art to variously employ the present invention.

By way of example, the bone, ligament, and bone-ligament constructs and systems and methods for their production according to the present invention are described with reference to the use of tissue harvested from rats. However, it is fully contemplated that tissue from any mammal, including human beings, could be similarly utilized according to the method described herein. The constructs, systems and methods of the present invention are not intended to be limited to one particular cell origin or age, construct shape or dimensions, time frame, component concentration, or culture condition. One skilled in the art can readily appreciate that various modifications can be made to the constructs, systems and methods described herein without departing from the scope of the invention disclosed.

Unless otherwise indicated, all solutions and media described herein may be prepared and stored at 4 C before, and then warmed to 37 C in a heated water bath immediately before use. It is understood that all reagent measurements, materials, submersion times, and other values described herein are approximate, and can be reasonably varied without affecting the method and resulting constructs. Furthermore, the approximate volumes of reagents within solutions described herein may be altered to provide a solution with reagents having similar volume ratios.

According to a first aspect of the present invention, a system and method are provided for producing self-organized, 3D bone tissue constructs solely from BMSC and their autogenous ECM, without the use of artificial, exogenous scaffolding. The system and method described herein bypass the many design challenges and limitations associated with the engineering of composite bone constructs with exogenous scaffolding. As described below, the successful fabrication of engineered bone constructs according to the present invention has been confirmed using histological and immunofluorescent markers for alkaline phosphatase activity, type I collagen, osteocalcin, and absence of type II collagen. The engineered tissues have been further analyzed structurally using transmission electron microscopy (TEM) and functionally with tensile tests.

BMSC are multipotent, mesenchymal stem cells that can differentiate into bone, cartilage, ligament, adipose tissue, and muscle (Alhadlaq and Mao, *Stem Cells Dev* 13: 436, 2004; Pittenger and Martin, *Circ Res* 95: 9, 2004) in response to chemical signals and generate and mineralize their own autogenous ECM. BMSC can be easily isolated from autologous sources and therefore serve as an attractive candidate for tissue engineering. Since a specific bone marker does not exist, an engineered tissue is characterized as being bone by a number of criteria. The presence of alkaline phosphatase, an enzyme that cleaves phosphate ions from organic molecules, is a precursor to mineralization of bone and thus an early sign of bone formation (Nauman et al., *Calcif Tissue Int* 73: 147, 2003). Bone is composed of predominantly type I collagen mineralized with hydroxyapatite crystals and contains osteocalcin, so the presence of these molecules further substantiates differentiation of BMSC towards bone. The absence of type II collagen, the predominant protein of cartilage, is often used to rule out differentiation to cartilage. The structural properties of bone including cells with an osteogenic morphology and nucleation and growth of mineralized structures through either matrix vesicles or intrafibrillar mineralization can be monitored using light and electron microscopy. The periosteum of bone is fibrous tissue found on the bone surface that contains fibroblasts, osteoprogenitor cells, and unmineralized type I collagen. Osteoprogenitor cells differentiate into osteoblasts during bone growth and remodeling. The periosteum can be identified through microscopy due to the elongated shape of fibroblasts and osteoprogenitor cells versus the round presentation of osteoblasts. The presence of rows of osteoblasts between the fibrous periosteum and the mineralized bone core is an indication of a functioning periosteum since the osteoprogenitor cells are actively differentiating to osteoblasts.

According to the present invention, BMSC isolation and expansion may be accomplished as follows. Under aseptic conditions, bone marrow may be collected from a bone of a host animal, such as the femur and tibia of female Fisher 344 rats. The soft tissues of the leg are removed from the femur and tibia, both ends of the bones are detached, and the marrow flushed out using a syringe (e.g., 25 gage needle) filled with Dulbecco's Modified Eagle Medium (DMEM; Gibco, Rockville, Md.). The marrow may be vortexed and then centrifuged at 480 g for ~5 minutes, such as using a ThermaForma General Purpose Centrifuge. The pellet may be resuspended in 10 ml growth medium (oGM), including DMEM with 20 volume % fetal bovine serum (FBS; Gibco), 6 ng/ml basic fibroblast growth factor (bFGF; Peprotech, Rocky Hill, N.J.), $10^{-8}$ M dexamethasone (dex; Sigma-Aldrich, St. Louis, Mo.), and 1% antibiotic-antimycotic (Gibco), and plated into tissue culture dishes (e.g., 100 mm diameter). The dishes may be kept in an incubator at 37° C., 95% humidity, and 5% $CO_2$. After ~48 h, the non-adherent cells may be removed by replacing the oGM with differentiation medium (oDM), further described below. The adherent BMSC are cultured to 80% confluence, at which time cells are enzymatically removed from the plate using a 0.25% trypsin-EDTA solution (Gibco) and passaged. Cells may be plated onto construct dishes within the third to fifth passages.

Tissue culture plastic dishes (e.g., 35 mm in diameter; BD Biosciences) may be filled with 1.5 ml SYLGARD® (type 184 silicone elastomer; Dow Corning Corp., Midland, Mich.) and serve as a substrate for construct formation. The polymer may be allowed to cure for approximately three weeks before use. The SYLGARD® may be coated with 3 mg/cm² natural mouse laminin (Invitrogen, Carlsbad, Calif.) by filling dishes with 3 ml of a 9.6 mg/ml laminin solution in Dulbecco's phosphate buffered saline (DPBS; GIBCO). The laminin solution may be evaporated overnight in a biosafety cabinet. Dishes are rinsed with DPBS and then filled with one ml of DMEM containing 20% FBS and 1% antibiotic-antimycotic. The dishes may then be sterilized via exposure to ultraviolet radiation (e.g., wavelength, 253.7 nm; bulb G30T8) in a biological safety cabinet for ~60 minutes, then kept in an incubator for 5-8 days prior to plating BMSC.

After the incubation, the medium is aspirated from the dish and BMSC may be seeded onto each dish in 2 ml oGM supplemented with 0.13 mg/ml L-ascorbic acid-2-phosphate (asc-2-phos; Sigma-Aldrich) and 0.05 mg/ml L-proline (Sigma-Aldrich). According to one aspect of the present invention, this formulation may result in 30 dishes in total with an initial cell density of 200,000 BMSC/dish. The cells may be fed oGM supplemented with asc-2-phos and L-proline every 2 days until confluence is reached. Once the cells reach confluence, two minuticn pins (e.g., 0.2 mm diameter and 1 cm long; Fine Science Tools, San Francisco, Calif.), may be pinned onto the cell monolayer in spaced relationship (e.g., 1.5 cm apart) to serve as anchors to constrain formation of the construct to a particular geometry. However, the pins are not required and do not constitute scaffolding as employed in prior art methods, as they may be used to define the endpoints of the construct, but the BMSC are not disposed therewithin.

Bone formation in vitro from BMSC may utilize osteogenic media including ascorbic acid, dexamethasone (dex), and an organic phosphate. Ascorbic acid maintains connective tissue and regulates ATPase, alkaline phosphatase, and protein synthesis in cultures of osteoblasts. Dex, a synthetic glucocorticoid, stimulates osteoblastic and adipogenic differentiation from BMSC. Phosphates provide phosphate ions for matrix mineralization. In addition to these nutrients, basic fibroblast growth factor (bFGF) and transforming growth factor beta (TGF-β) contribute to bone development in vitro but are not required for osteogenic differentiation from BMSC. bFGF, commonly used as a potent mitogen for many types of mesenchymal cells, increases mineralization, alkaline phosphatase activity, and the concentrations of bone specific markers such as calcium and osteocalcin when administered to BMSC in an osteogenic medium (Scutt and Bertram, *Calcif Tissue Int* 64: 69, 1999; Lisignoli et al, *Biomaterials* 22: 2095, 2001). TGF-β regulates osteoblast replication and migration, increases alkaline phosphatase activity, and stimulates collagen production and matrix maturation in bone cultures derived from both osteogenic cells and BMSC (Locklin et al., *Cell Biol Int* 23: 185, 1999).

At confluence, the oGM is switched to a second, differentiation medium (oDM) which may comprise DMEM with 7% horse serum (Gibco), 0.13 mg/ml asc-2-phos, 0.05 mg/ml L-proline, and 2 ng/ml transforming growth factor beta (TGF-β; Peprotech) to induce construct formation. The oDM may be changed every 2-3 days until the constructs are to be used.

Seven days after 3D construct formation, the engineered bone constructs (ESC) according to the present invention were mounted on a holder using tissue freezing medium (Triangle Biomedical Sciences, Durham, N.C.) and immersed in −80° C. isopentane. The frozen samples were sliced longitudinally to a thickness of 9-12 mm using a Microm HM 500 cryostat system. The slides were then used for either histological staining for light microscopy or immunofluorescent staining. For histochemical staining, tissue sections were fixed with methanol and stained for either calcification with Alizarin Red or hematoxylin and eosin to observe tissue structure. The remaining sections were fixed in acetone and stained for alkaline phosphatase activity.

Immunofluorescent staining was performed to detect the presence of collagen I, collagen II, and osteocalcin. Frozen sections were fixed with methanol for 5 min and rinsed 3 times with DPBS. Sections were then blocked for 30 min with Ham's F-12 containing 5% donkey serum (DS; Jackson ImmunoResearch Labs, Inc, West Grove, Pa.) at 37° C. Sections were then incubated for 2 h with the primary antibodies in Ham's F-12 containing 1% DS. The concentrations of each of the antibodies were as follows: 5 mg/ml of rabbit anti-rat collagen I (Abcam Inc., Cambridge, Mass.), 5 mg/ml of mouse anti-rat collagen II (Calbiochem, Darmstadt, Germany), and 10 mg/ml of mouse anti-rat osteocalcin (Abeam). Samples were then rinsed 3 times with Ham's F-12 and were blocked again in Ham's F-12 containing 5% DS at 37° C. for 10 min. The secondary antibodies (5 mg/ml) were then applied to the sections for 1 h as follows: Alexa Fluor 488 donkey anti-rabbit IgG (Molecular Probes, Eugene, Oreg.) for collagen I, Alexa Fluor 555 donkey anti-mouse IgG (Molecular Probes) for collagen II, and Alexa Fluor 488 donkey anti-mouse IgG (Molecular Probes) for osteocalcin. A Nikon Eclipse TS100 microscope equipped with an X-Cite 120 Fluorescence Illumination System was used to image the histochemically and immunofluorescently marked sections. Controls were performed for the immunofluorescent staining (data not shown). Images were captured using a Diagnostic Instruments Spot Insight Color camera.

Samples were fixed for TEM in 2.5% glutaraldehyde (Electron Microscopy Sciences, Hatfield, Pa.) in 0.1 M Sorensen's buffer, pH 7.4, for 24 h at 4° C. Constructs were thoroughly rinsed with Sorenson's buffer, and post fixed with 1% osmium tetroxide in Sorensen's buffer for 2 h. Samples were then rinsed with double distilled water and stained with 8% uranyl acetate in double distilled water for 1 h. Constructs were dehydrated in a graded series of ethanol, treated with propylene oxide, and embedded in Epon 812. Longitudinal ultra-thin sections, 70 nm thick, were prepared and stained with uranyl acetate and lead citrate. The sections were examined using a Philips CM100 electron microscope at 60 kV. Images were digitally recorded using a Hamamatsu ORCA-HR digital camera system operated using AMT software (Advanced Microscopy Techniques Corp., Danvers, Mass.).

Tensile tests were performed on EBG engineered in vitro according to the present invention either 7 days (n=4) or 6 weeks (n=3) after 3D construct formation. Tests were performed using a custom tabletop tensiometer attached to a Nikon SMZ1500 dissection microscope. The constructs were immersed into a bath of DPBS and the ends were grasped by clamps. The dimensions of the construct were measured prior to each test for a cross-sectional area calculation using a reticule in the eyepiece of the microscope. Beads 25 mm in diameter (Interactive Medical Technologies; Irvine, Calif.) were brushed on the surface of the construct as position markers for digital image correlation (DIC) analysis of tensile strain. Constructs were stretched at a strain rate of $0.01\ s^{-1}$. Force was measured using a custom force transducer and monitored using LABVIEW software (National Instruments, Austin, Tex.); the resolution of the force transducer used for testing the EBC was 1 mN. Images of the construct were captured using a Basler camera attached to the Nikon dissection microscope at a frequency of $2.5\ s^{-1}$ during the test to follow the location of the DIC markers. The bead position from each image was recorded using LABVIEW software with a resolution of 5 mm and length between beads was calculated by subtracting the position of one bead from another. Nominal stress was calculated using the equation $\sigma=F/A_0$ where $\sigma$ is nominal stress, F is force, and $A_0$ is the initial cross-sectional area of the sample. Nominal strain was calculated using the equation $\epsilon=(l-l_o)/l_o$, where $\epsilon$ is the nominal strain, l is the current length between beads, and $l_o$ is the original length. Moduli were obtained by calculating the slope of the tangent of stress versus strain plots at the maximum strain prior to failure.

Seven days after 3D construct formation, EBC were placed into a piece of sterile TYGON® silicone tubing (United States Plastics Corp., Lima, Ohio) that had inner and outer diameters of 1.6 and 3.2 mm, respectively, and a length of 1.5 cm. Fisher 344 rats were anesthetized using 0.001 ml Nembutal sodium solution (pentobarbital sodium injection; Ovation Pharmaceutical Inc., Deerfield, Ill.) per gram of the animal. The silicone tubes containing the constructs were then implanted between the biceps femoris and the quadriceps of the left leg of the host animals. The silicone tubing was used in order to identify the engineered tissue during explantation.

Four weeks after implantation, constructs were removed from the animal. The diameter of the explants was measured using electronic calipers. The samples were then either frozen and mounted in tissue freezing medium and stored at −80° C. or fixed in 2.5% glutaraldehyde and mounted in paraffin for histological studies.

Wide angle X-ray diffraction (WAXS) was performed on EBC (n=2) samples according to the present invention 6 weeks in culture post 3D construct formation. The EBC samples were removed from their medium and allowed to dry. The EBC samples were then placed on a single-crystal silicon substrate and examined with a Bruker D8 Discover diffractometer using Cu Kα radiation and a source voltage of 40 kV. The samples were investigated over a 2q range of 23-55° with 20 counts recorded/degree. Scattering resulting from the substrate was subtracted and resulting peaks were identified using the hydroxyapatite Powder Diffraction File from the Joint Committee on Powder Diffraction Standards (JCPDS; Swarthmore, Pa.) (Hydroxyapatite Reference XRD peaks (ICDD: 01-073-0293)).

As described above, in accordance with the system and method of the present invention, BMSC are cultured on construct dishes in a medium that induces osteogenic differentiation (oGM). Approximately 2-4 days after plating, the cells reach confluence and are switched to a second medium (oDM) containing a lower serum concentration and TGF-β, and two minutien pins are attached to the culture dish as constraint points. After a sufficient amount of ECM is produced, the tissue monolayer lifts from the substrate and contracts radially. The placement of the two constraint points inhibits full contraction and the monolayer self-organizes into a cylindrical tissue construct dependent on the placement of any minutien pins which, according to one aspect of the present invention, may be about 1.5 cm in length and an elliptical cross section with major and minor axes of 1.0±0.07 mm and 0.78±0.13 mm, respectively (FIG. 1a). EBC formation according to the present invention is complete within ~14 days of plating the BMSC onto the cell culture dishes. The resulting engineered tissue is completely solid, which suggests that the cells within the EBC remodel the tissue during and after construct formation. The EBC were kept in culture either 7 days or 6 weeks after formation of 3D structure prior to being fixed for histological and structural characterization.

Figure 1B:
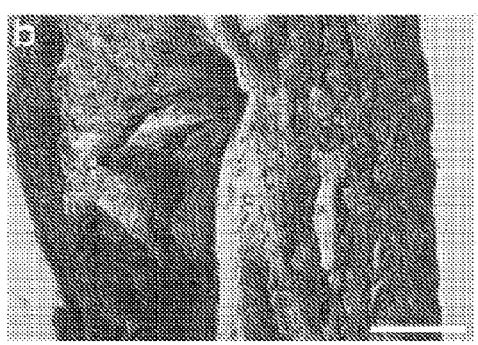
FIGS. 1b-1e depict staining of an EBC according to the present invention for (b) hematoxylin and eosin; (c) alkaline phosphatase; (d) alizarin red for calcification; and (e) collagen I (scale bars=250 mm)
Figure 1C:
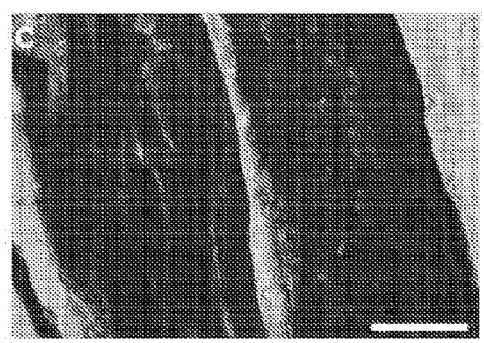
Figure 1D:
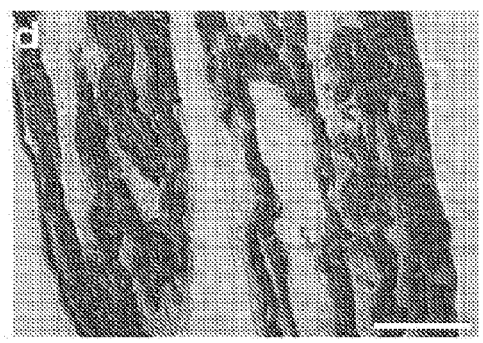
Figure 1E:
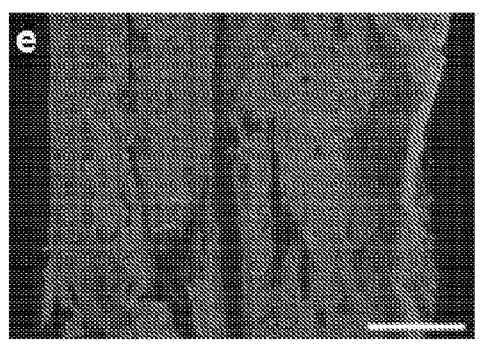
Figure 2A:
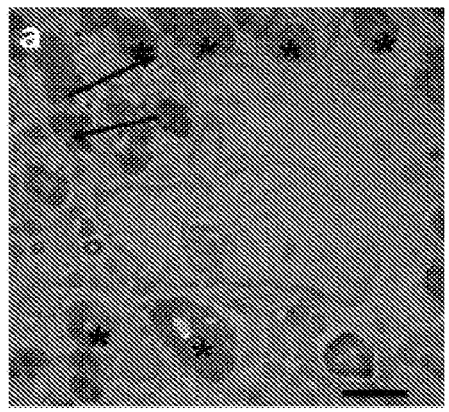
Figure 2B:
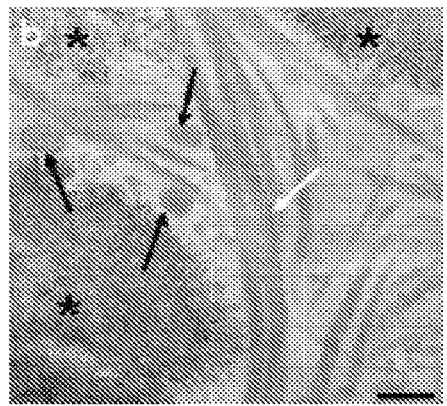
Figure 2C:
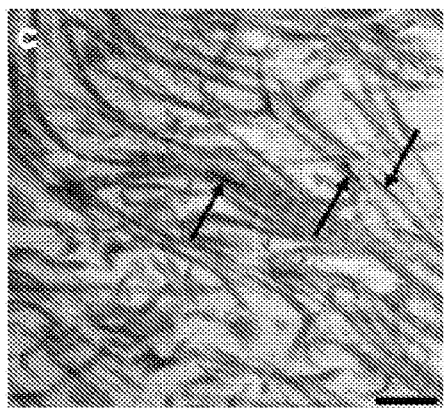
Figure 2D:
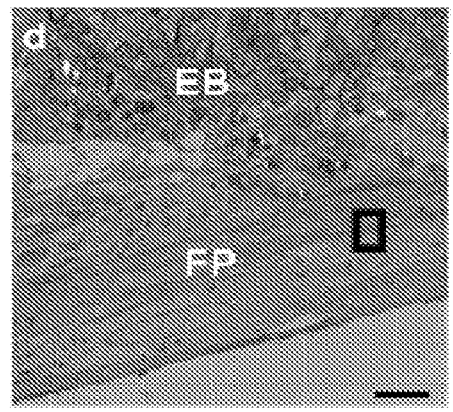
FIG. 2d illustrates the edge of the engineering bone (EB) having a fibrous periostuem (FP) as indicated by fibroblasts (scale bar=4 mm)
Figure 2E:
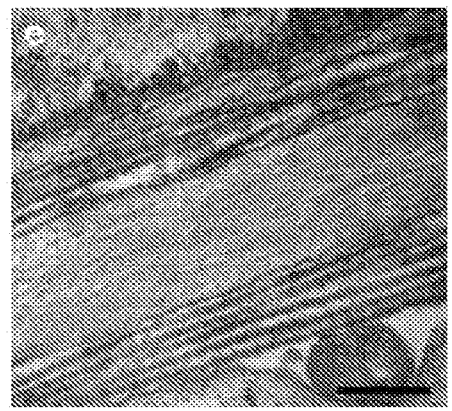
FIG. 2e is an expansion of the boxed area of FIG. 2d which shows that the collagen between the fibroblasts in the (FP) lacked mineral crystals (scale bar=300 nm)
Figure 3:
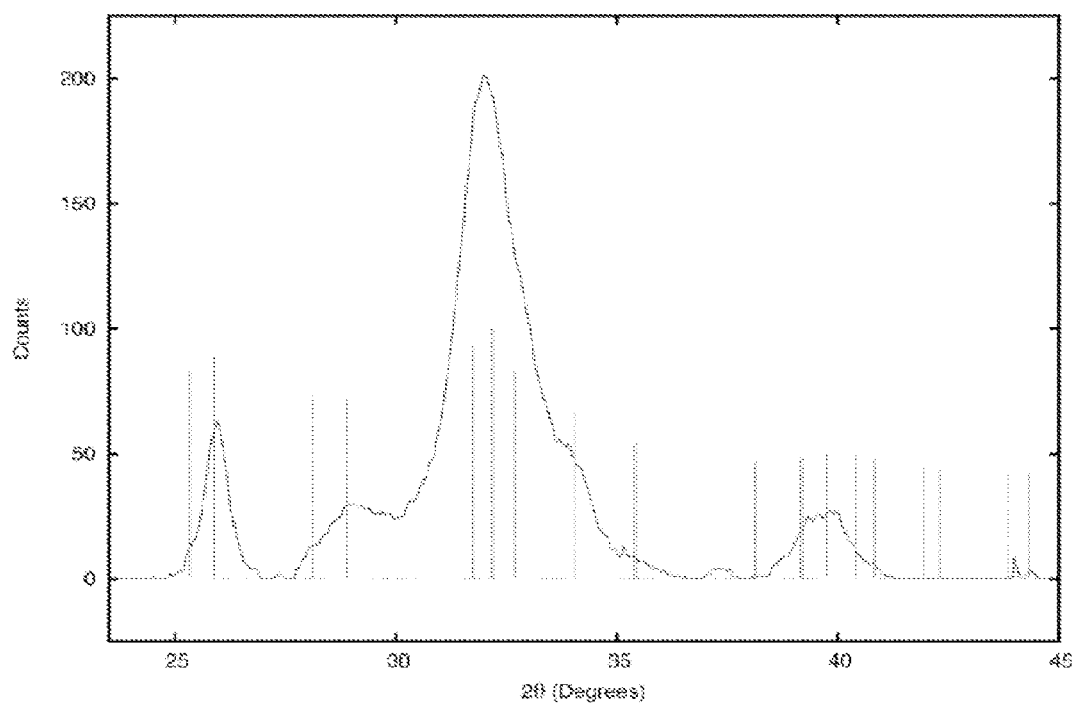
FIG. 3 depicts a wide angle x-ray diffraction (WAXS) pattern of the EBC according to the present invention, showing that the mineral is hydroxyapatite when compared with peak locations and relative intensities for the hydroxyapatite standard.

At 7 days post 3D EBC formation, hematoxylin and eosin (H and E) staining revealed that the self-assembled EBC were composed of both dense and fibrous regions (FIG. 1b). The bulk of the tissue stained positively for alkaline phosphatase activity (FIG. 1c), and calcium deposits were located throughout the samples as seen by Alizarin Red staining (FIG. 1d). The EBC according to the present invention stained intensely throughout for type I collagen (FIG. 1e) and lacked type II collagen (data not shown), which is consistent with the constitution of native bone. At this point, the EBC lacked osteocalcin (data not shown). TEM verified that the EBC contained osteoblasts (FIG. 2a) in a collagenous matrix undergoing mineralization. The diameter of the collagen was 29±4. nm which corresponds to the diameter of type I collagen found in the femur (Ameye and Young, *Glycobiology* 12: 107R, 2002). Mineralization was noted to occur through both matrix vesicles and intrafibrillar calcification (FIGS. 2b-c). The onset of periosteum development was observed by the presence of fibroblasts and axially aligned unmineralized type I collagen on the periphery of the EBC (FIGS. 2d-e). Wide angle X-ray scattering (WAXS) diffraction peak locations for the EBC corresponded with those of hydroxyapatite verifying that the crystals seen in the TEM micrographs were indeed hydroxyapatite (FIG. 3).

The EBC according to the present invention were able to maintain their size and shape after pins were removed from the edges. When the constructs were grabbed by forceps at their centers, they were able to resist deformation under the pinching loads of the forceps, and the EBC resist compressive and bending deformation. Tension tests performed on EBC in culture at 7 days and 6 weeks post 3D EBC formation revealed maximum tangent moduli of 7.5±0.5 MPa (n=4) and 29+9 MPa (n=3), respectively. The cross-sectional area remained the same between 7 days and 6 weeks post 3D construct formation. The tangent moduli are normalized with respect to the cross-sectional area of the EBC; therefore, the increase of stiffness between the two time points appears to be a measure of EBC phenotype development, and not of physical growth.

Figure 4A:
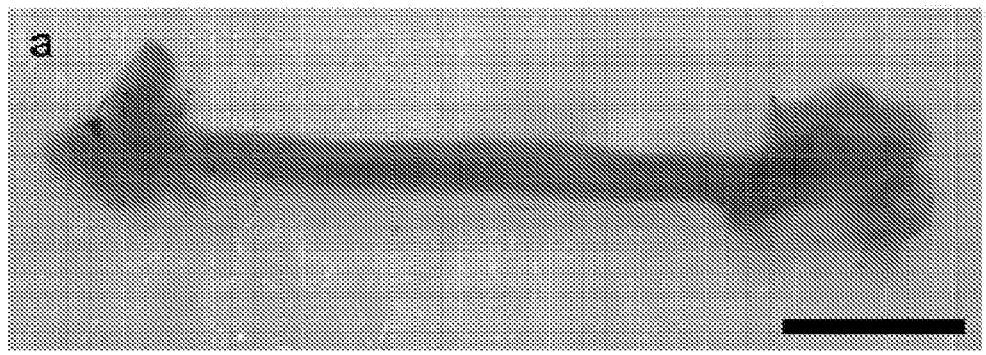
FIG. 4a is a photograph of an EBC explant according to the present invention after a 4 week implantation (scale bar=5 mm)
Figure 4B:
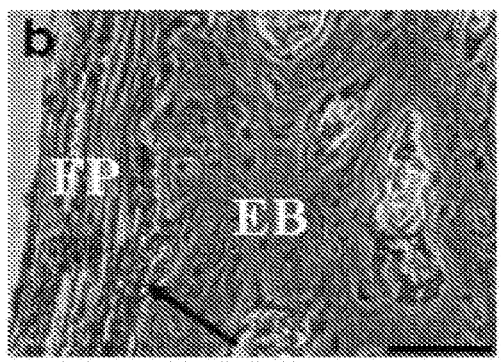
FIGS. 4b-c illustrate H and E stains of (b) an edge of a demineralized explant, wherein fibrous periosteum (FP) is seen on the edge of the sample, along with osteoblasts (arrow) differentiating from osteoprogenitor cells of FP and invading engineered bone (EB), and (c) the center of a demineralized engineered bone which shows osteocytes (black arrows) and blood vessels (white arrows) (scale bar=62.5 mm)
Figure 4C:
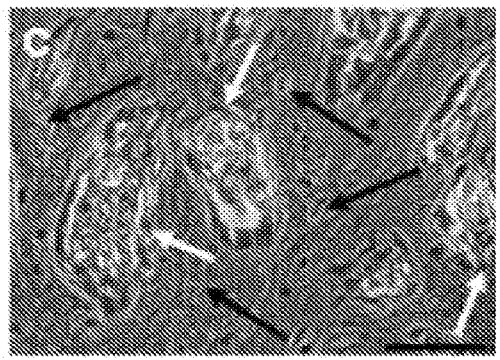
Figure 4D:
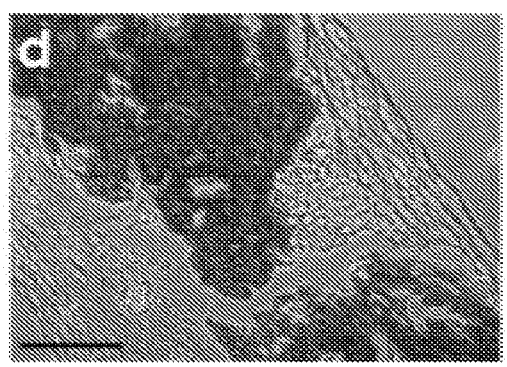
FIGS. 4d-e depict EBC explants stained for (d) calcification using Alizarin red and (e) collagen I (scale bar=250 mm)
Figure 4E:
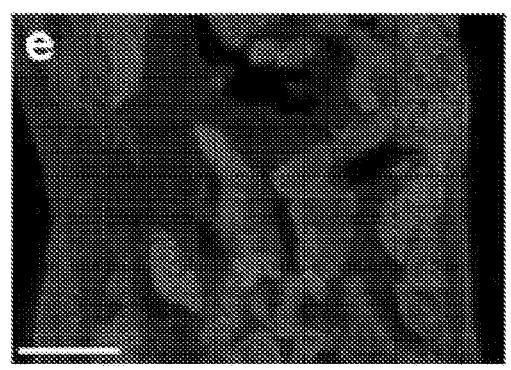

At 7 days post 3D construct formation, the EBC were implanted for 4 weeks between the biceps femoris and quadriceps of Fisher 344 rats. While implanted, the EBC grew and remodeled so that the resulting explant was cylindrical with a circular cross section. The diameter of the explant was 1.6±0.3 mm, equaling the inner diameter of the silicone tubing they were placed in during implantation (FIG. 4a). H and E staining of the demineralized explants revealed a structure that appeared similar to that of native bone (FIGS. 4b-c). Osteocytes in lacunae and blood vessels were seen throughout the construct (FIGS. 4b-c). Further development of a periosteum-like structure was seen following implantation, as indicated by the fibrous tissue along the edge of the bone explants and the neighboring osteoblast-like cells (FIG. 4b). Alizarin Red staining of explant sections showed increased amounts of calcification (FIG. 4d) when compared to those of the construct engineered in vitro (FIG. 1d). The explanted constructs contained type I collagen (FIG. 4e) and lacked type II collagen (data not shown). After implantation, osteocalcin was also evenly distributed throughout the bone explants (data not shown).

Figure 5A:
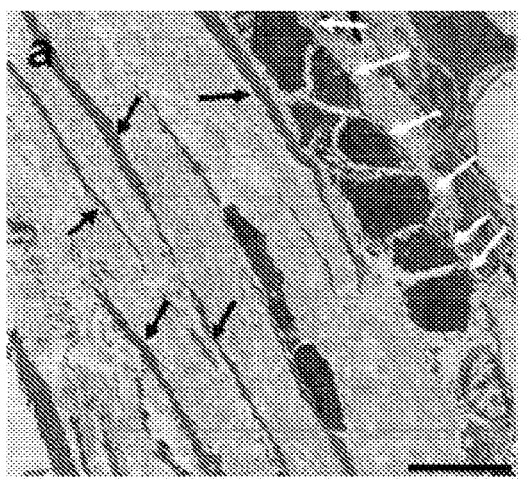
Figure 5B:
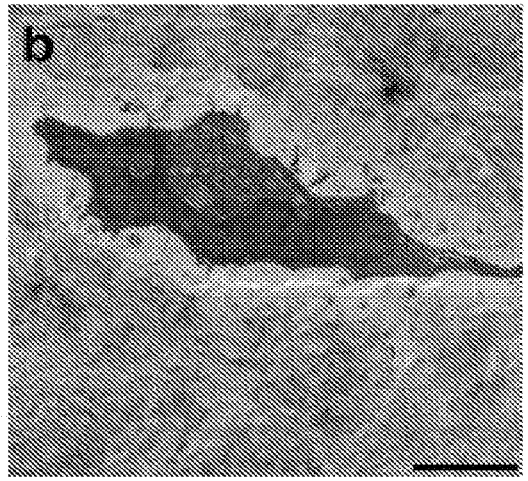
Figure 5C:
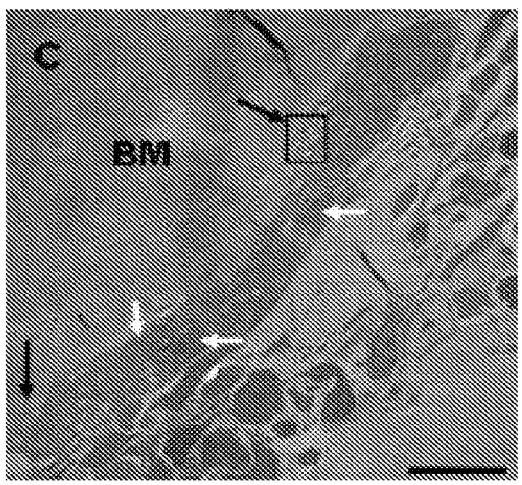
Figure 5D:
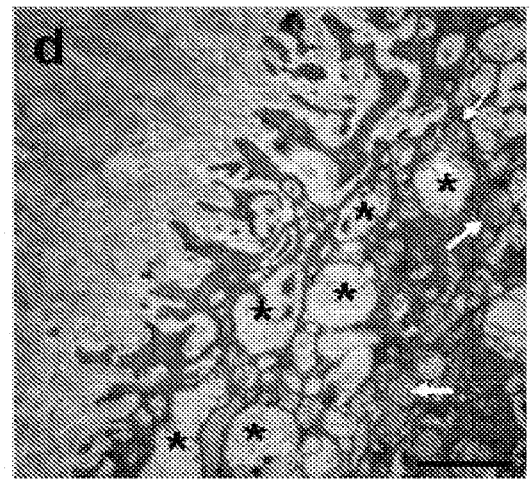

TEM of the demineralized explants showed a periosteum-like structure containing osteoprogenitor cells and rows of osteoblast-like cells (FIG. 5a). This structure is similar to that of native bone in which osteoblasts differentiate from progenitor cells within the periosteum in rows and migrate towards the bone matrix. Osteocytes in lacunae were seen within the bone matrix (FIG. 5b). Osteoclasts were found throughout the mineralized tissue region (FIGS. 5c-d). The osteoclasts were identified via their multinucleation (FIG. 5c), ruffled borders, and a plethora of vacuoles used by the cell for storage of resorbed material (FIG. 5d).

Therefore, the system and method according to the present invention produce 3D bone constructs which self-organized in osteogenic media from only BMSC and their autogenous ECM, without disposing the cells within an exogenous scaffold. The development of a periosteum-like structure in EBC in vitro as described herein has not been reported in 2D bone nodules or in bones engineered using exogenous scaffolding. The presence of a periosteum-like structure is also significant since it indicates both fibrogenic and osteogenic differentiation from a single cell source within the same culture environment. This suggests that the BMSC were differentiating due to the cues delivered through the medium and preferentially as a result of their location within the construct.

After 7 days post 3D construct formation, the EBC exhibit alkaline phosphatase activity and are composed of mineralized type I collagen enclosed within a fibrous periosteum-like tissue. The mechanical properties of the EBC according to the present invention improved over time in vitro; tangent stiffness increased by a factor of four over a five-week period. No significant physical size change occurred in vitro from 7 days to 6 weeks in culture after 3D construct formation, indicating phenotype development due to tissue remodeling or increased collagen or mineral production. After 4 weeks in vivo, the EBC grew to equal the size of the tubing it was placed into prior to implantation, and the phenotype of the EBC according to the present invention continued to advance during implantation in vivo. The explants contained a vascularized bone structure with osteoblasts, osteocytes and osteoclasts. The explants also contained osteocalcin which was not present before implantation and qualitatively stained more intensely for mineralization. The explants also had a functional periosteum-like tissue containing osteoprogenitor cells that were undergoing differentiation to osteoblasts. The observation of osteoprogenitor cells actively differentiating into osteoblasts as well as the presence of osteoclasts demonstrates that the EBC actively grew and remodeled in vivo in a manner similar to that of native bone.

The addition of bFGF to the culture medium according to the present invention may allow for monolayer formation rather than the formation of bone nodules. The mitogenic effects of bFGF in addition to dex in the present invention may have increased proliferation, thus allowing for monolayer formation rather than the formation of nodules. TGF-β may be the factor that controls 2D versus 3D construct formation. Although the overall effects of this growth factor on BMSC are not fully known, it is generally used in culture to stimulate collagen production, matrix maturation, and to induce chondrogenic differentiation from BMSC. TGF-β may increase the rate of collagen production at an early stage of EBC development and prior to full osteogenic differentiation.

The tangent moduli of the EBC according to the present invention at 7 days and 6 weeks in culture post 3D construct formation were 7.5±0.5 MPa and 29±9 MPa, respectively. Previous studies have reported the moduli of unmineralized and mineralized embryonic bone as 1.11 MPa and 117 MPa, respectively (Tanck et al., Bone 35: 186, 2004). The mechanical properties of the EBC are consistent with developing native bone since the moduli lie within the limits of native embryonic bone. The tangent modulus is a measure of constitutive stiffness and is independent of construct size; the increase in EBC tangent moduli between 7 days and 6 weeks in culture post 3D construct formation therefore may be an indication of phenotype advancement rather than physical growth.

The system and method of engineering bone-like structures according to the present invention, in which cells are cultured to secrete, assemble, and mineralize their own three dimensional scaffolding, bypasses the complexity of engineering a scaffold and shifts the paradigm of bone tissue engineering to the guided self-assembly of an autogenous extracellular matrix. Furthermore, the system and method described herein utilize the culture of BMSC that can be isolated from autologous sources without major ethical issues, and may be used clinically with minimal risk of rejection. The EBC according to the present invention provides a functional periosteum around an engineered bone, thus further advancing the state of bone engineering. This system and method to engineer bone tissues can be used as a heuristic approach to tissue engineering for large bone defect repair or replacement without the use of an exogenous scaffold and as a model for bone formation through intramembranous ossification.

These scaffold-less bone constructs not only contribute significantly to the field of bone engineering, but also to the field of stem cell research. In the system and method described herein, osteogenic and fibroblastic differentiation of BMSC resulted within the same culture environment, suggesting that stem cells may differentiate due to mechanical signals and cues from their location relative to other cells in an engineered construct in addition to chemical signals. Mechanically constraining the contractile monolayer induces tensile strain along the major axis of the constructs and preferentially orients the collagen fibers in this direction. The constructs according to the present invention are the first 3D, scaffold-less tissues developed from BMSC that demonstrate phenotype advancement in vitro and in vivo.

An additional goal of tissue engineering is to fabricate tissue for use in repair of tissue damaged as a result of disease, trauma and surgery, especially for cases where the amount of bone loss creates a critical defect which will not repair by normal self-repair processes and needs intervention. In further accordance with the present invention, utilization of the EBC to repair a critical bone defect may produce a new bone segment in which the engineered construct will incorporate into the host bone and form a viable interface that will restore the functionality.

According to another aspect of the present invention, using multiple EBC, larger, more complex bone shapes may be fabricated such as, but not limited to, a femur or mandible bone in a rat. Multiple bone constructs may be arranged laterally or longitudinally with respect to one another during in vivo implantation and this arrangement may allow the constructs to grow and remodel into a cohesive construct. The present invention further contemplates the use of imaging technologies to visualize a healthy contralateral bone, generate a three-dimensional mold (e.g., silicone) from that image, obtain BMSC from the patient (e.g., from the pelvic bone) needing the tissue replacement, and fabricate an engineered bone for replacement from the patient's own BMSC.

Figure 6A:
Figure 6B:
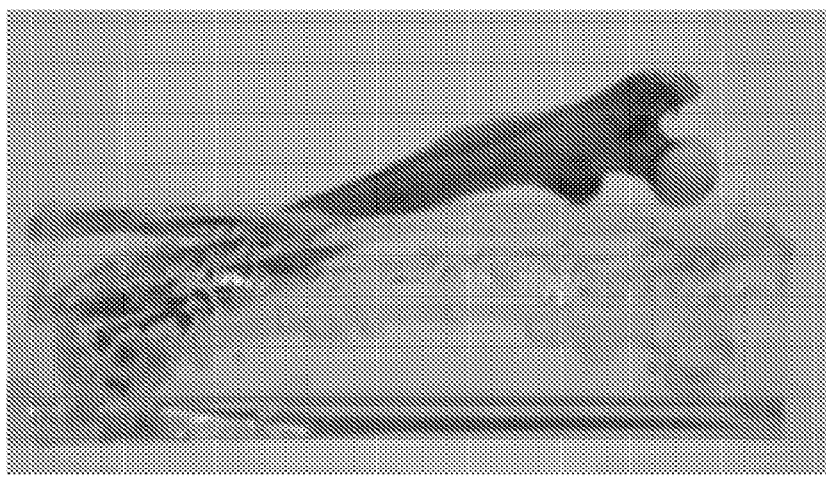
Figure 6C:
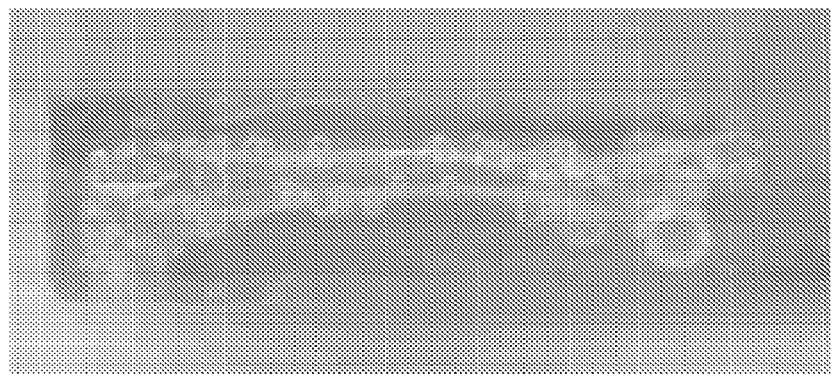

Bone molds may be constructed according to the present invention by submerging native rat bones (e.g., femur, tibia, pelvis, mandible) into silicone as it cures (FIG. 6). The bones may be dissected out of the rat and, after thoroughly drying, the bones may be sprayed with silicone mold release and suspended in liquid SYLGARD®. The SYLGARD® may be allowed to cure for approximately one week. The native bone may then be removed from the silicone, leaving a mold in the shape of native bone.

Bone monolayers may be fabricated as described herein. Approximately one week after shifting to oDM, when the forming bone constructs have lifted from the substrate and have started to roll up (e.g., ~20%), the constructs may be implanted into molds and then into the host animals. In one example, a plurality of forming bone constructs (e.g., three) may be placed into a mold. The constructs may be secured together, such as by suturing, the ends of the constructs may be secured to the mold, and the mold may be secured inside the host animal to prevent migration of the mold within the host. In preliminary experiments utilizing the system and method according to the present invention, suturing three constructs together prior to implantation visually yielded one fused construct.

In further accordance with the present invention, BMSC may be used to fabricate 3D scaffold-less ligament and bone-ligament constructs. The ability of BMSCs to differentiate into a specific lineage in vitro may be controlled by the culture environment, differentiation-inducing agents, growth factors and mechanical stimulation. Previous attempts have been made to create 3D ligaments in vitro using artificial scaffolding, but these have met with limited success because of the difficulty in creating a construct that is biologically compatible with the in vivo environment and integrates with bone tissue.

Figure 7A:
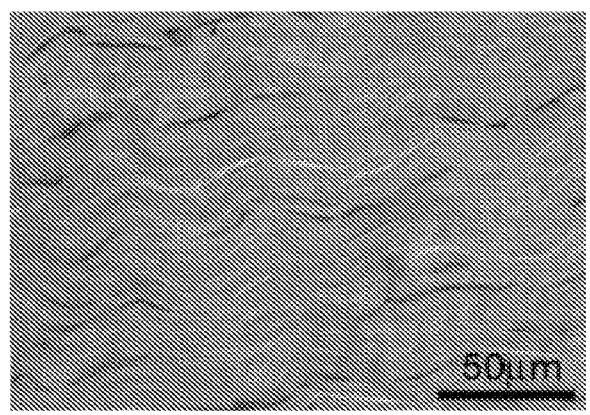
FIGS. 7a-c illustrate a native adult rate medial collateral ligament (MCL) after (a) H & E staining; (b) immunostaining with collagen type I; and (c) immunostaining with elastin C.
Figure 7B:
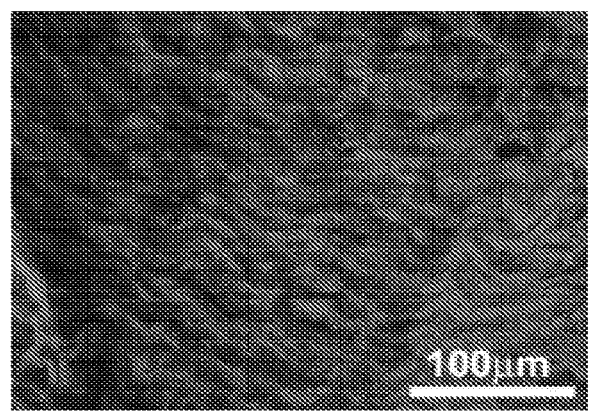
Figure 7C:
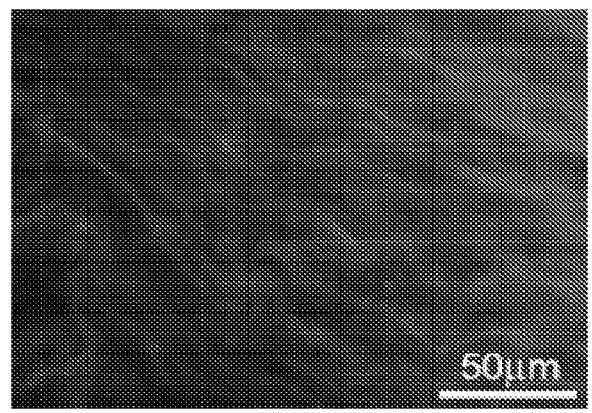

As a matter of background, mature ligament obtained from rat medial collateral ligament (MCL) shows the characteristic wavy pattern of collagen fibrils with elongated cell nuclei dispersed amongst the fibrils (FIG. 7a). Immunohistochemical staining of longitudinal sections of native MCL reveals positive staining for collagen I (FIG. 7b) and elastin (FIG. 7c), and negative staining for collagen II (image not shown).

According to the present invention, self-organized 3-D ligament constructs (ELC) may be engineered from BMSC in fibrogenic media. With reference to the system and method for producing EBC described above, for ligament the growth medium (fGM) includes Fetal Bovine Serum (FBS, Gibco BRL Cat#10437-028), 6 ng/ml basic fibroblast growth factor (bFGF; Peprotech, Rocky Hill, N.J.), 0.13 mg/ml asc-2-phos, 0.05 mg/ml L-proline, 5 ml A9909 (Sigma A9909), and differentiation medium (fDM) includes 460 ml DMEM with 35 ml 100% Horse Serum Albumin (HSA, Gibco BRL Cat#16050-122), 0.13 mg/ml asc-2-phos, 0.05 mg/ml L-proline, 2 ng/ml transforming growth factor beta (TGF-β; Peprotech), and 5 ml A9909 (Sigma A9909). Once the cells become confluent, pins may be inserted in the substrate in spaced relationship to guide and constrain the resulting construct geometry.

As described above, since BMSC are multipotent cells that can differentiate into a plurality of tissue types, several markers are used to identify tissues in the developing constructs according to the present invention. Type I collagen, fibronectin and elastin immunostaining are used as markers of ligament development. Staining for type II collagen, aggrecan and tenascin-C are used as markers of the developing interface between bone and ligament (enthesis). Morphological observations of cellular and ECM structures using light and electron microscopy may be used to identify the presence of the expected cell and tissue types in the developing constructs.

Figure 8A:
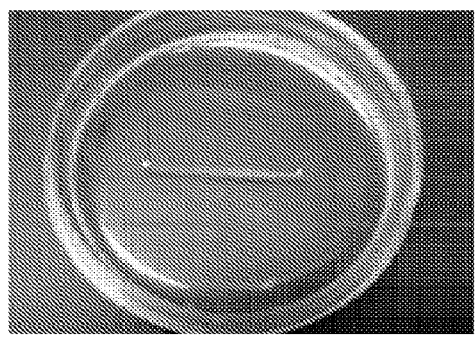
FIGS. 8a is a photograph of a three-dimensional ligament construct according to the present invention.
Figure 8B:
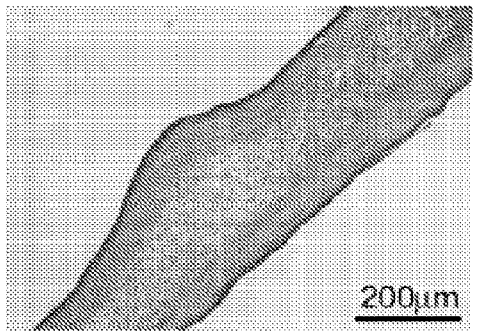
FIGS. 8b-c depict H & E staining of a section taken from the mid-section of a ligament construct according to the present invention at two different magnifications.
Figure 8C:
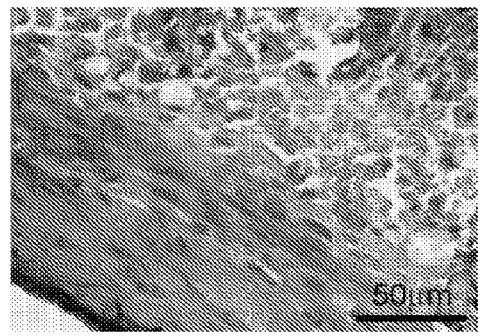
Figure 8D:
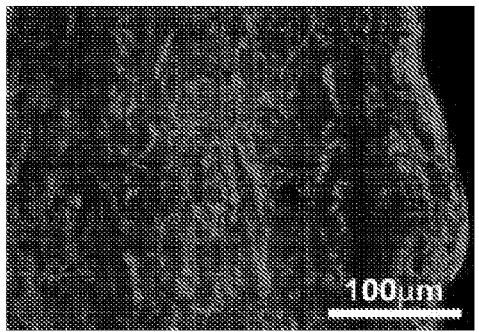
FIG. 8d depicts immunostaining of a mid-section of a ligament construct according to the present invention with collagen type I.

With reference to FIG. 8a, approximately 3 days after detachment of the monolayer, the cells self organized into a cylinder, wherein the length of the construct was determined by the placement of the pins (e.g., 15 mm) and, the diameter in the image shown was approximately 500 µm. In vitro engineered ligament according to the present invention has an outer perimeter that looks similar to native ligament with highly organized collagen and elongated nuclei between fibril (FIGS. 8b-c). Immunohistochemistry of the ELC indicates that the fibrillar perimeter is type I collagen (FIG. 8d). In contrast to the ECM formed by the BMSC in osteogenic media, the engineered ligament ECM lacks mineralization as determined by an absence of alizarin red staining, does not stain for alkaline phosphatase activity, and lacks type II collagen (negative staining data not shown). The tensile response of the engineered ligament is non-linear and viscoelastic; the response to cyclic loading shows strain softening. The as-formed engineered ligaments have a tangent stiffness of 2.8±1.8 MPa (n=3). After four weeks of implantation, the ligament explants grew physically in size and their tangent stiffness increased by about an order of magnitude to 15.4±5.6 MPa (n=3). Native adult rat MCL has a tangent stiffness of 550±50 MPa (n=2).

Preliminary mechanical tests of the ELC according to the present invention show that the constructs have the same nonlinear poroviscoelastic characteristics of native MCL. The use of exogenous scaffolds as in prior art methods often results in mechanical function that does not include these characteristics, whereas the constructs according to the present invention have the organized extra-cellular matrix proteins, proteoglycans and fluid phases of native tissue.

To be most useful for tissue replacement, the ELCs need an anchoring mechanism that will allow functional attachment to the bone in the location of the ligament replacement. Therefore, an engineered ligament with engineered bone at each end would be optimal for repair if the engineered bone integrates with the native bone in vivo following implantation. According to the present invention, a system and method are provided for co-culturing self-organized 3D ligament tissue from BMSC with engineered scaffold-less bone tissue to form bone-ligament-bone (BLB) constructs having a mechanically viable enthesis to withstand the transmission of physiological strains.

Figure 9A:
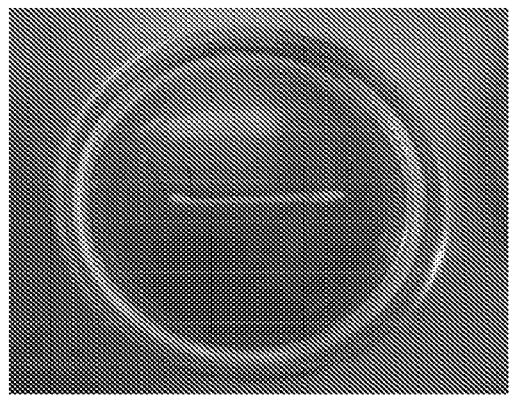
FIGS. 9a-c are photographs of bone-ligament-bone (BLB) constructs engineered in an unchambered culture dish (a) and a chambered culture dish (b-c) in accordance with the present invention.

BLB construct formation according to the present invention may be accomplished in different ways. According to one aspect of the present invention, the fGM may be removed from previously prepared laminin-coated plates and 2 ml of a cell suspension containing $2\times10^5$ cells per ml of fGM may be plated in each culture dish and placed in a 37° C. 5% $CO_2$ incubator, wherein the medium may be changed every 2-3 days. After the cells become confluent, approximately 3 days later, engineered bone tissue fabricated as described above and having some degree of confluence may be cut into segments (e.g., 5 mm in length) and placed in contact with the cell monolayer. According to one aspect of the present invention, the bone constructs may be pinned (e.g., using two minutien pins) on top of the cell monolayer facing each other so that the inner ends are spaced apart (e.g., 1 cm). At this point, the fGM may be replaced by fDM. The ligament monolayer is allowed to roll up and at least partially surround each of the bone monolayers, creating a functional integration of the bone with the ligament and forming a 3-D, self-organized BLB construct (FIG. 9a). Of course, it is understood that a bone-ligament construct having bone at only one end is also fully contemplated according to the present invention.

Figure 9B:
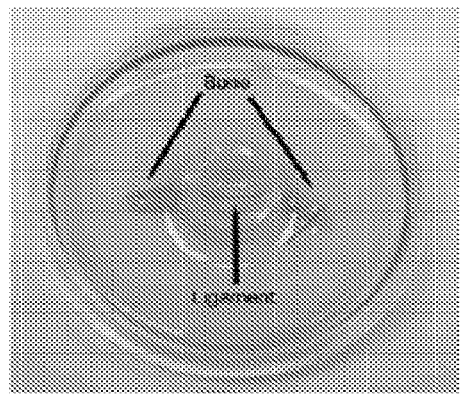
Figure 9C:
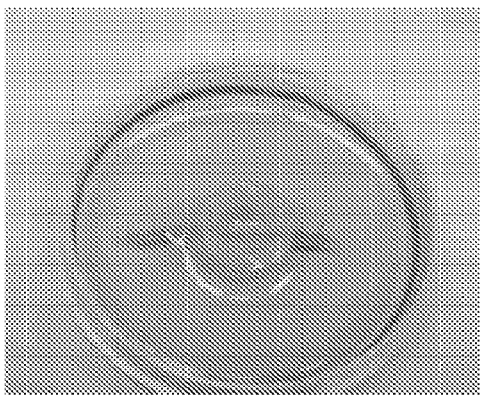

The effect of the ligament DM (fDM) on continued bone formation is unknown. Preliminary data suggest that the bony ends of the co-culture continue to develop bone matrix and produce osteocytes once the bones have formed, even if the medium is no longer supplemented with dex. A chambered cell culture dish (FIG. 9b) may be utilized to allow bathing of the ligament portion of the construct in fDM while exposing the bone portions of the construct in bone DM (oDM). At the time of ELC formation, it is unknown if osteogenic precursor cells remain (FIG. 9c). If bone precursor cells do exist, in further accordance with the present invention, a fully formed ligament construct may be placed into a chambered culture dish with the interior chamber exposed to fDM and the outer chambers to oDM to create a BLB construct in this manner.

One of the most common sites for ligament damage and thus need for repair is the anterior cruciate ligament (ACL). Due to the poor healing capacity of the ACL following injury, surgical "reconstructions" or replacements of the ligament, involving bone/ligament autografts or allografts, are performed at a rate of 400,000 per year. In all replacement methodologies, the utilization of screws to fix the bony plug of the graft to the native bone is not a permanent solution. Immune rejection or physical dislodging of the screw means a second surgical intervention to reattach the graft. The accessibility of the ACL especially in small animal models such as the rat limits the usefulness of the ACL for studies of ligament replacement. Therefore, the MCL has been used herein as a model to demonstrate the ability of the engineered BLB constructs according to the present invention to incorporate into endogenous bone tissue, and to grow and remodel in vitro and in vivo. Utilization of the BLB as an MCL replacement may result in incorporation of the bone segment of the BLB into the host bone and formation of a viable connection that will restore the functionality of the knee joint.

A representative example of a 3D BLB construct fabricated according to the present invention is shown in FIG. 10a, wherein the construct length in this case is 15 mm with a width of 1 mm, although it is understood that BLB construct dimensions are not limited by this example. Five days following 3-D formation, the BLB construct was used to replace the MCL in a rat. During implantation, the native MCL was excised, holes were drilled at the place of enthesis in both the femur and tibia (FIG. 10b), a BLB was inserted into a silicone tube for subsequent identification during explanation, and secured into place with 7-0 suture (FIG. 10c). Alternatively, the bone sections of the construct may be secured by suturing the construct to the surrounding connective tissue. One month later, the entire knee was extracted from the animal (FIG. 10d), the engineered construct was isolated from surrounding tissues, and the patellar, ACL, PCL, and LCL were excised leaving the BLB-based MCL replacement tissue adhered to the femur and tibia (FIG. 10e). Following 1 month implantation, the BLB construct fused with the bone at both the femur and tibia and increased in size, stiffness and strength, and the native MCL has been replaced by the remodeled BLB construct. The bones were then anchored into a tensiometer and the mechanical properties of the explanted BLB were measured (FIG. 12).

Figure 11A:
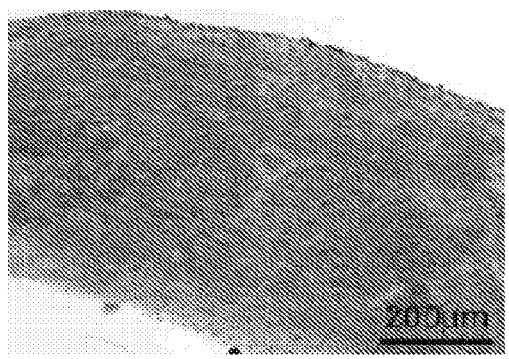
Figure 11B:
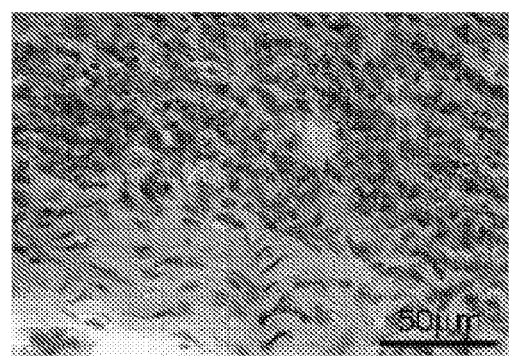
Figure 11C:
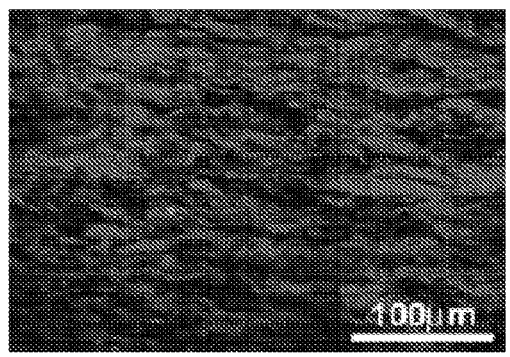
Figure 11D:
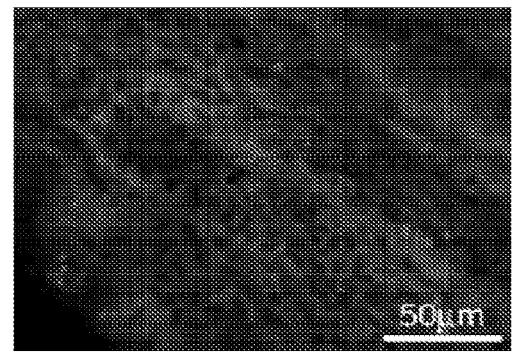

Longitudinal sections were taken through the mid section of the BLB-based MCL replacement explant and stained with H and E. FIG. 11 reveals collagen fibrils filling the entire cross-section of the explant, while the collagen content resembles that of adult MCL, there are many more nuclei present amongst the fibrils (FIGS. 11a-b). Immunohistochemical staining of the sections shows positive staining for both collagen I (FIG. 11c) and elastin (FIG. 11d) similar to the staining pattern observed in native adult MCL (FIG. 7).

Figure 12A:
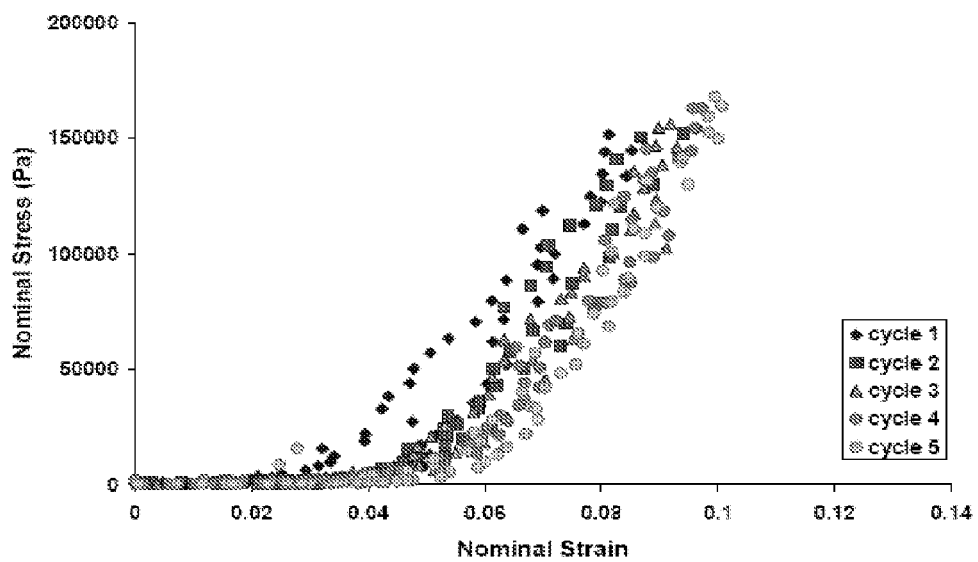
FIGS. 12a-c are graphs of nominal stress vs. nominal strain data for BLB constructs according to the present invention before (a) and after (b) one month implantation for MCL replacement, and data for native MCL (c).
Figure 12B:
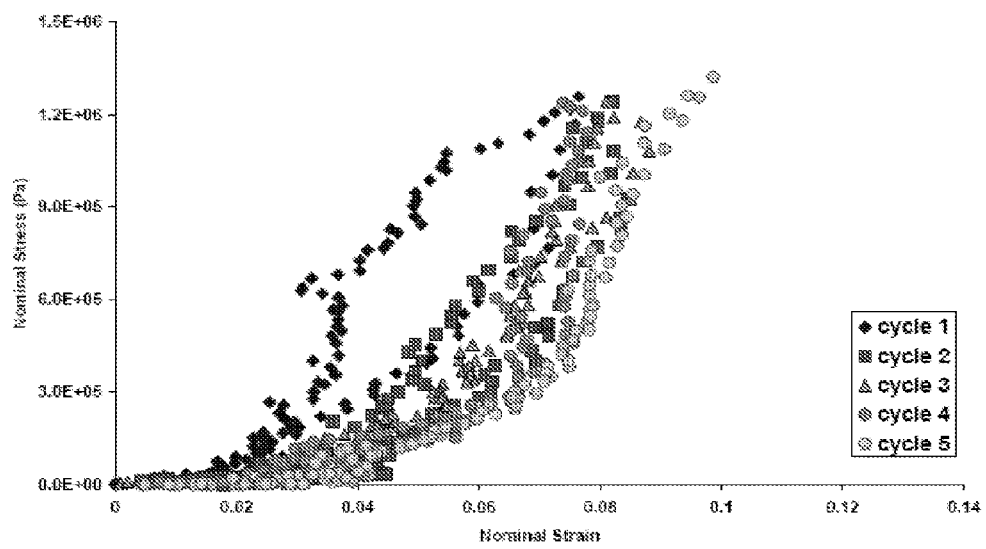
Figure 12C:
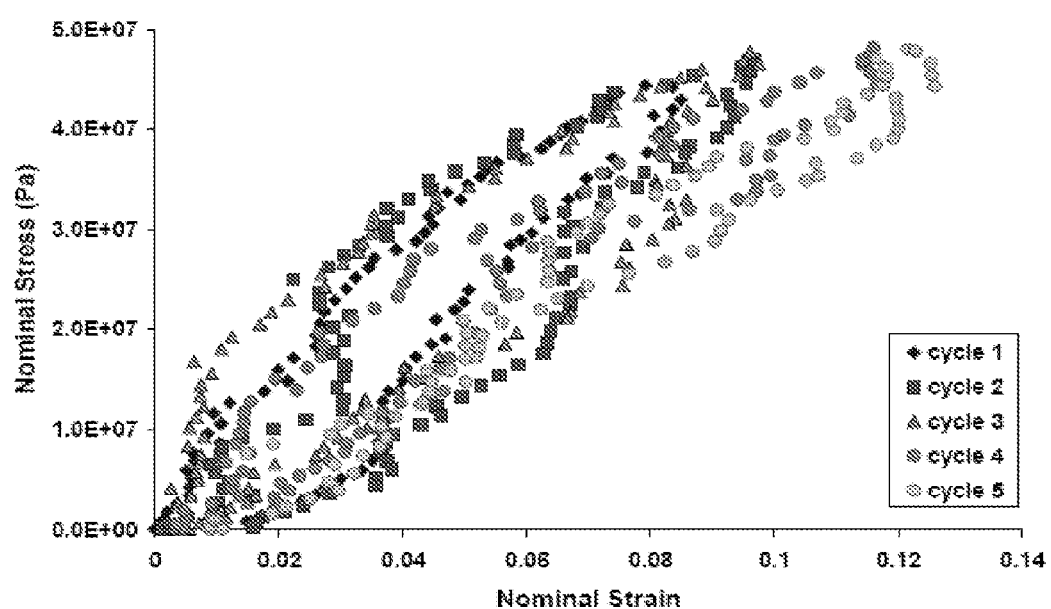

Using a custom-designed and built tensiometer for soft tissue testing that includes digital image correlation measurements of sequential local tissue positions to accurately calculate actual tissue strain, several load-unload cycles were conducted to examine the viscoelastic response of in-vitro BLB constructs (FIG. 12a), BLB explants (FIG. 12b) and native adult rat MCL (FIG. 12c). The tangent stiffness is computed as the slope of the first load cycle at a strain of 0.06. The in vitro constructs have a ligament tangent stiffness of 2.8±1.8 MPa (n=3). The phenotype development within the ligament region of the BLB during one month of implantation is seen by comparing FIGS. 12a and 12b. The toe region in the in vitro BLB construct (FIG. 12a) becomes less pronounced during implantation (FIG. 12b). The cyclic response shows the engineered tissue in vitro is non-linear and viscoelastic with hysteresis in each load-unload cycle (FIG. 12a). The BLB retains these same characteristics as its mechanical stiffness increases by about an order of magnitude during one month of implantation (FIGS. 12b) to 15.4±5.6 MPa (n=3). The native adult MCL exhibits the same mechanical response to cyclic loading and is roughly an order of magnitude stiffer (550±50 MPa (n=2)) than the explanted BLB constructs (FIG. 12c).

Therefore, the co-culture of engineered ligament and bone tissues according to the present invention generates 3D cylindrical BLB constructs with the morphological characteristics of bone and ligament in vivo and a mechanically viable enthesis that structurally and biochemically resembles that of neonatal tissue. The creation of an engineered bone/ligament co-culture with a viable interface in vitro greatly expands the potential for ligament repair by providing a functional enthesis to bone. In vivo implantation of EBCs and BLBs according to the present invention may further advance the phenotype and functionality of the bone, ligament and enthesis, and these engineered constructs may be viable treatments for tissue repair or replacement. The fabrication of engineered BLB constructs according to the present invention with the capability for growth and remodeling of the ligament and permanent incorporation of the engineered bone into the surgical site may vastly improve the lifespan of the surgical repair, for example, of a damaged ACL.

The development of a BLB construct as in the present invention that has a structurally sound enthesis offers innumerable implications for future investigations on bone and ligament development. For example, the BLB construct may be used to investigate basic science questions such as the effects of various growth factors—dexamethasone, basic fibroblast growth factor, transforming growth factor beta, bone morphological proteins, etc.—on osteogenesis, fibrogenesis and enthesis formation. The BLB construct may also be used to investigate the effect of genetic manipulation via null vs. over-expression of specific cytoskeletal proteins or osteogenic regulatory factors on the bone development, or to investigate the effects of various mechanical loading protocols in vitro and in vivo on bone and ligament development.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A bone-ligament-bone construct, comprised from: bone marrow stromal cells provided on a substrate without disposing the cells in an exogenous scaffold; the cells cultured in vitro in fibrogenic medium comprising ligament growth medium such that the cells form a confluent ligament monolayer; and two bone constructs in contact with the confluent monolayer in ligament differentiation medium such that the monolayer detaches from the substrate to at least partially surround each bone construct and functionally integrate therewith, thereby forming a three-dimensional bone-ligament-bone construct, and wherein the ligament differentiation medium includes a lower serum concentration compared with the ligament growth medium.

2. The bone-ligament-bone construct of claim 1, wherein the monolayer is constrained by at least two anchors secured thereto; and the bone construct is provided in contact with the monolayer.

3. The bone-ligament-bone construct of claim 1, wherein the bone and ligament form an enthesis at the bone-ligament interface.

4. The bone-ligament-bone construct of claim 1, wherein the bone-ligament-bone construct is cylindrical.

5. The bone-ligament-bone construct of claim 1, wherein the bone-ligament-bone construct is compliant.

6. The bone-ligament-bone construct of claim 1, wherein the bone portion of the construct exhibits mineralization and/or alkaline phosphatase activity.

7. The bone-ligament-bone construct of claim 1, wherein the bone and ligament portion include type I collagen.

8. The bone-ligament-bone construct of claim 1, wherein the ligament portion does not exhibit mineralization.

9. The bone-ligament-bone construct of claim 1, wherein one bone end is removed to form a bone-ligament construct.

10. A scaffold-free, three dimensional bone-ligament-bone construct, comprised from: bone marrow stromal cells provided on a substrate without disposing the cells within an exogenous scaffold, wherein the cells are cultured in vitro in ligament growth medium such that the cells form a confluent monolayer and detach from the substrate to form a self-organized three-dimensional bone-ligament-bone construct when in co-culture in a ligament differentiation medium, wherein the ligament differentiation medium includes a lower serum concentration compared with the ligament growth medium.

11. The scaffold-free bone-ligament-bone construct of claim 10, further comprising at least two anchors secured to the substrate and the confluent monolayer in spaced relationship to constrain development of the three-dimensional bone-ligament-bone construct.

12. The scaffold free bone-ligament-bone construct of claim 11, wherein one bone end is removed to form a bone-ligament construct.

13. A method for repairing a damaged enthesis comprising implanting a bone-ligament-bone or bone-ligament construct of claim 1 into a subject in need thereof.

14. The method of claim 13, wherein the damaged enthesis is a bone-ligament enthesis.

15. The method of claim 14, wherein the ligament is an anterior cruciate ligament (ACL), a medial collateral ligament (MCL) or a posterior cruciate ligament (PCL).

16. The method of claim 13, wherein the bone section of the construct is inserted into holes drilled into native bone and secured to native bone or surrounding connective tissue.

17. A method for repairing a damaged enthesis comprising implanting a bone-ligament-bone or bone-ligament construct of claim 10 into a subject in need thereof.

18. The method of claim 17, wherein the damaged enthesis is a bone-ligament enthesis.

19. The method of claim 17, wherein the ligament is an anterior cruciate ligament (ACL), a medial collateral ligament (MCL) or a posterior cruciate ligament (PCL).

* * * * *